United States Patent
Nozaki et al.

(10) Patent No.: US 8,518,693 B2
(45) Date of Patent: Aug. 27, 2013

(54) TEMPERATURE REGULATING MEMBER

(75) Inventors: Takayuki Nozaki, Chiba (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 1129 days.

(21) Appl. No.: 12/188,408

(22) Filed: Aug. 8, 2008

(65) Prior Publication Data
US 2009/0078395 A1 Mar. 26, 2009

(30) Foreign Application Priority Data
Sep. 20, 2007 (JP) .................. 2007-243219

(51) Int. Cl.
C12M 1/00 (2006.01)
C12M 3/00 (2006.01)
F28D 15/00 (2006.01)

(52) U.S. Cl.
USPC .......... 435/307.1; 435/289.1; 435/303.3; 165/104.22; 165/104.21; 165/109.1

(58) Field of Classification Search
USPC .......... 435/289.1, 303.3, 307.1; 165/104.21, 165/104.22, 109.1
See application file for complete search history.

(56) References Cited

U.S. PATENT DOCUMENTS

| | | | |
|---|---|---|---|
| 4,850,966 A * | 7/1989 | Grau et al. ............. | 604/82 |
| 5,451,524 A * | 9/1995 | Coble et al. ........... | 435/284.1 |
| 2001/0055799 A1 * | 12/2001 | Baunoch et al. ....... | 435/286.5 |
| 2002/0011496 A1 | 1/2002 | Inaba et al. | |
| 2003/0072687 A1 * | 4/2003 | Nehring et al. ........ | 422/102 |
| 2006/0191282 A1 | 8/2006 | Sekiya et al. | |
| 2010/0009335 A1 * | 1/2010 | Joseph et al. .......... | 435/3 |

FOREIGN PATENT DOCUMENTS

| | | |
|---|---|---|
| JP | 11-113560 | 4/1999 |
| JP | 2006/232331 | 9/2006 |

* cited by examiner

Primary Examiner — Nathan Bowers
(74) Attorney, Agent, or Firm — Brundidge & Stanger, P.C.

(57) ABSTRACT

A temperature regulating member for avoiding a deterioration in heat radiating output efficiency and deterioration in buffering occurring due to a non-uniform heat distribution within the heat storage material. Heat non-uniformities within the heat storage material are eliminated by inserting one or multiple agitating tools inside the heat storage material by generating an agitating current occurring due to use of agitator tools whose relative positions change within the heat storage material during shipping.

9 Claims, 9 Drawing Sheets

TEMPERATURE REGULATING MEMBER

CLAIM OF PRIORITY

The present application claims priority from Japanese patent application JP 2007-243219 filed on Sep. 20, 2007, the content of which is hereby incorporated by reference into this application.

FIELD OF THE INVENTION

This invention relates to a heat storage material for effectively maintaining the specified temperature of cells, etc.

BACKGROUND OF THE INVENTION

Temperature conditions cause fluctuations to occur in the stress on cells such as cells serving as biological samples. Therefore some type of temperature regulation is required in most cases when transporting samples such as cells. Demands are made for example to transport cells at 36° C. which is higher than normal outdoor temperatures and close to body temperature. There are multiple types of culture vessels for holding cells and certain shipping methods must be used according to the shape of the culture vessel. Cells typically tend to adhere to the bottom of the culture vessel, and culture vessel shapes are in dish or plate shapes. In the case of suspended cells, the cells float while suspended in the culture solution and a tube-shaped container is used to ship these suspended cells. This tube container is a vertically long structure. If this tube container is placed horizontally during shipping, then the culture medium adheres to the lid of the culture contained and becomes a likely cause of biological contamination. The culture vessel must therefore be maintained in a suitable position during shipping according to the vessel shape. Tube type culture vessels must be maintained in a vertical (standing) position.

Heat storage materials have been reported containing hydrocarbons (paraffin, etc.) that induce a phase transition from a liquid to a solid state at approximately 36° C. (See JP-A-2006-232331, for example.).

Methods in the related art for controlling the temperature of the liquid phase substance include a technique for installing a magnetically rotated agitator in the container holding the fluid (See for example JP-A-1999-113560.). In this technique, an agitator is affixed in the container holding the fluid substance, the agitator magnetically rotated to induce an agitating current, for supplying a uniform culture medium.

SUMMARY OF THE INVENTION

Besides functioning heat source during covering and shipping of culture vessels containing cells, the heat storage material also possesses a buffering function due to its liquid state. The environmental temperature of the sample can be maintained at approximately 36° C. for a long time by enclosing this heat storage material with insulating material and storing it within an outer container (This structure is hereafter called a portable homothermal container.).

When shipping the culture vessels containing cells etc., covered with a heat storage material whose sealed interior contains hydrocarbons (paraffin, etc.) for inducing a phase transition from the liquid state to solid state at approximately 36° C., the heat storage material radiates heat from the external circumferential section in contact with outer air at a temperature lower than the internal section. The heat storage material therefore gradually hardens from the liquid state starting from the outer circumferential section. The heat storage material at this time starts hardening from the outer circumferential section as the heat is radiated away. The heat discharge (or radiating) efficiency is proportional to the temperature differential between the outer air and the outer circumferential section of the heat storage material so that as the outer circumferential section of the heat storage material cools and the temperature differential becomes smaller, the heat discharge efficiency drops, and heat remains within the interior of the heat storage material. The time that the internal temperature is maintained within the portable homothermal container consequently becomes shorter. Moreover, the outer circumferential section of the heat storage material quickly hardens so that the buffering function is lost.

In many cases when shipping tube culture vessels containing suspended cells, the tube culture vessels must be maintained in an upright state during shipping in order to avoid biological contamination. Tube culture vessels are long in the vertical direction so the heat storage material needed for covering the outer circumference of the culture vessel must also be a structure that is long in the vertical direction.

When creating an agitating current inside the heat storage material, the heat storage material whose heat was lost to the outer circumference is immediately taken into to the interior of the heat storage material. The heat distribution within the heat storage material consequently becomes uniform and there is no hardening of molecules just at positions on the outer circumferential section. Therefore, the cooling and hardening of just the outer circumferential section can be avoided as long as there is an agitating current. The buffering function can also be maintained.

In the method disclosed in JP-A-1999-113560, the agitator tool formed beforehand is magnetically rotated and causes an agitating current within the heat storage material. However, the heat storage material covering the culture vessel is a structure long in the upright (vertical) direction when shipping tube culture vessels. The agitator tool is in this case located on the bottom of the heat storage member so the agitating current occurs from the bottom surface, and a sufficiently strong agitating current does not occur upwards in the heat storage material. In other words, the upper part of the heat storage material is not agitated, and is cooled and hardened by the outer air. The lower part on the other hand is kept sufficiently agitated. The temperature differential between the upper section and lower section of the heat storage material consequently widens, and an uneven internal temperature distribution occurs within the tube culture vessel.

In order to provide a motive force to rotate the agitator tool, a magnetic agitator and its drive device are required for generating a rotating magnetic field. Even if the interior of the portable homothermal container for shipping the cells, contained this drive device, the portable homothermal container would need a large amount of space so that temperature regulation would be impossible. Moreover, an electrical drive device would no longer operate if the storage battery failed or the electrical circuits broke down so that ensuring reliable operation during shipping was impossible. Therefore for the above reasons, the temperature must be regulated during shipping, even for tube culture vessels long in the upright (vertical) direction; moreover the maintenance of buffering functions and heat discharge efficiency in the heat storage material must be improved by utilizing a small, light-weight and low-cost member.

The following aspects are proposed to resolve the problems of the background art.

An agitator tool that basically does no react with the heat storage material is installed in the interior of the heat storage material. More specifically, one or multiple agitator tools having a certain mass and size are installed beforehand in interior of the heat storage material. This agitator tool may also have a shape that allows easily changing its position relative to the heat storage material during shipping. The agitator tool may be made from a material that essentially does not react with the hydrocarbons sealed within the heat storage material, and capable of moving smoothly without any mutual reaction. This agitator tool may be able to easily change its relative position in the heat storage material by way of motion such as the tilt, vibration, or swaying naturally applied to the portable homothermal container. The change in position by the agitator tool induces an agitating current in the sealed liquid hydrocarbons that achieves a uniform distribution of heat. Paraffin which is a saturated chain hydrocarbon general in the form of $C_nH_{2n+2}$ may for example be utilized. In particular, n-Eicosane which is expressed chemically as $C_{20}H_{42}$ and has a melting point of 36.4° C. is used here.

This invention yields the effect that the agitating current occurring in the upper section in the heat storage material the same as in the lower section so that a uniform heat distribution is achieved regardless of whatever position is vertical. The internal temperature of the heat storage material is uniform so the problem of early cooling and hardening of upper section can be avoided. Moreover the buffering function can be maintained for a long time since the outer circumferential section can be maintained in a liquid state for a long period of time. Still further, an agitating current is efficiently induced within the heat storage material during shipping even when transporting tube culture vessels that are long in the vertical direction.

DETAILED DESCRIPTION OF THE PREFERRED EMBODIMENTS

Figure 1:
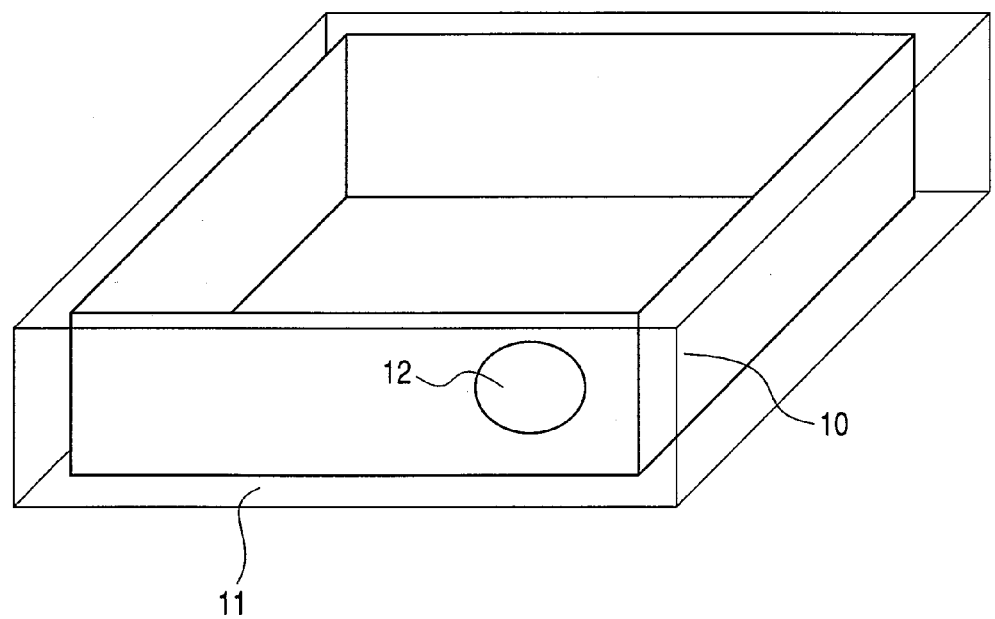
FIG. 1 is an overall view of the heat storage material and one agitator tool.

The embodiments of this invention are described next while referring to the drawings. FIG. 1 shows the structure of the heat storage material and the agitator tool. FIG. 1 is an overall view of the temperature regulating member made up of the heat storage material, the agitator tool installed in the interior of the heat storage material, and the container for holding the heat storage material and agitator tool. A container 11 is provided for holding (sealing in) the solidified hydrocarbon (n-Eicosane) 10 utilized as the heat source, and the sphere-shaped agitator 12 is installed inside the interior of that container. The shape of the container is for example is shown as a rectangular parallelepiped. The agitator tool is installed so as to make contact with the hydrocarbons. The agitator tool surface possesses properties that essentially do not react with the heat storage material. Materials such as glass and steel can be used.

Figure 2:
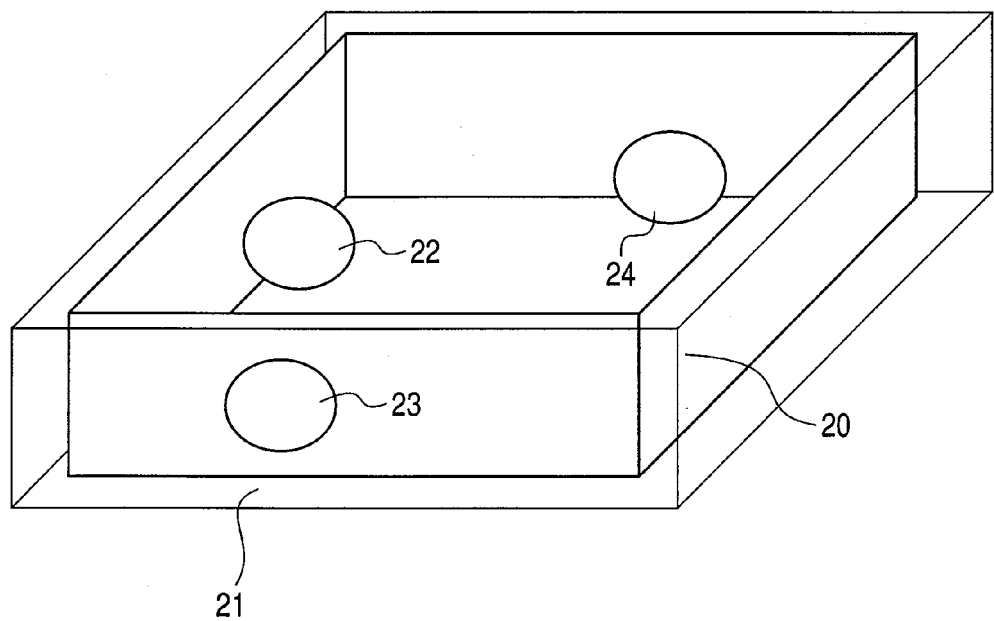
FIG. 2 is an overall view of the heat storage material and three agitator tools.

FIG. 2 is an overall view of the temperature regulating member made up of the heat storage material, multiple agitator tools (in this embodiment, 3 agitator tools) installed in the interior of the heat storage material, and the container for holding the heat storage material and agitator tools. Three agitator tools 22, 23, 24 are installed in the container in the structure of the heat storage material shown in FIG. 1. Multiple agitator tools can be installed but in this example three agitator tools are used.

Figure 3:
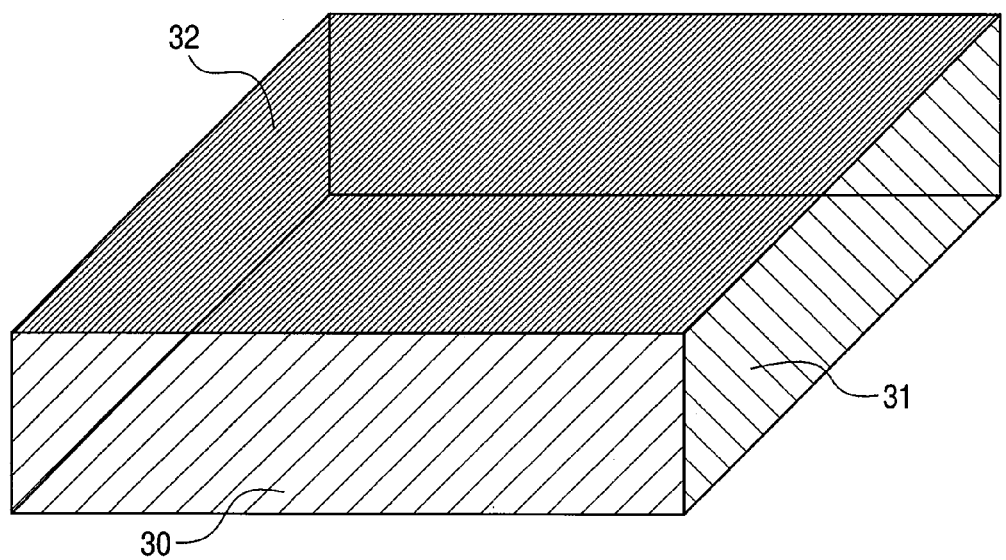
FIG. 3 is an overall structural view showing the heat storage material for improving the heat propagation characteristics and the agitator tool.

FIG. 3 is a drawing showing, among the containers holding the heat storage material, a heat propagation member 30 made from material possessing high heat propagation characteristics serving as the section making contact with the culture vessel storing the cells; and the insulating member 31 as the remaining section for enhancing the heat discharge efficiency. In the structure of the heat storage material shown in FIG. 1, the container 11 has been changed to combine a high heat propagation film 30 serving as a heat propagation member possessing high heat transfer, with a high heat insulating member 31. The container structure is made up of the high heat propagation film 30 and the heat insulator wall 31. During shipping (transport), the upper part of the high heat propagation film 30 is in contact with the culture vessel holding the cells, and heat propagates via the high heat propagation film 30 to maintain the temperature of the culture vessel at approximately 36° C. At all other locations, the insulating effect of the heat insulator wall 31 suppresses the discharge of heat. A wasteful discharge of heat is prevented in this way. An agitator tool 32 is installed in the interior of the container. In this figure one agitator tool is used but multiple agitator tools (for example, 3) may be installed the same as shown in FIG. 2.

Figure 4:
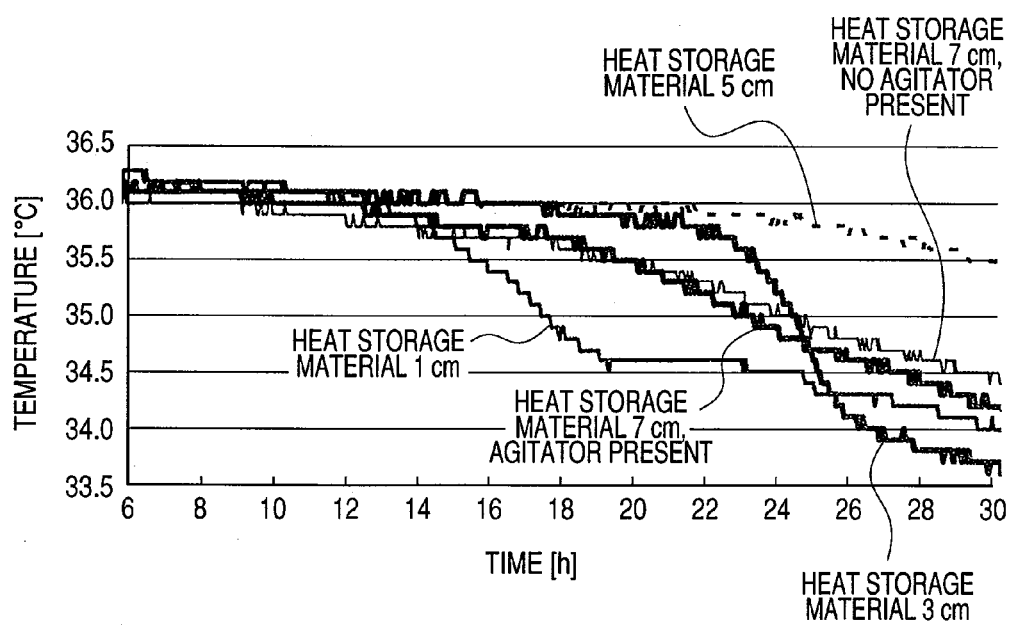
FIG. 4 is a graph for assessing temperature fluctuations over elapsed time when the agitator tool and heat storage material height ratios were changed.

FIG. 4 is drawings showing an example of fluctuations as the temperature drops along with dissipation of heat from the heat storage material over elapsed time when the agitator tool and heat storage material heights are changed. In this example, one agitator tool as a sphere with a diameter of approximately 1.6 cm was installed. The material of this agitator tool was glass. Here, n-Eicosane which is expressed chemically as $C_{20}H_{42}$ and has a melting point of 36.4° C. is utilized as the hydrocarbons sealed within the container and serving as the heat storage material. The agitator tool and the heat storage material do not react with each other, and the agitator tool is capable of smooth movement. The bottom surface of the container holding the heat storage material was circular and approximately 4.5 cm in diameter, and the heat storage material in the container was set at heights of 1, 2, 3, 4, 5, 6, and 7 cm. A container holding heat storage material with a height of 7 cm and with no agitator tool inserted was utilized as the control. In the above described structure, heat storage material was heated beforehand to 45° C. by a thermostat to liquefy the hydrocarbons to form a liquid, and then was placed in a state where a rotational motion and gentle gradient were applied under an outside temperature of 32° C. This rotational motion and gentle gradient served as a model for the motions sustained during shipping. During this period, the temperature sensor measured the temperature fluctuations in the upper part of the heat storage material, and changes overtime in the upper section temperature as well as the state of the hardened heat storage material were assessed.

Under all conditions, the heat storage material was heated in advance by the thermostat to 45° C., the temperature quickly lowered after exposure to an outside temperature of 32° C., and reached a fixed state at the melting point of the sealed hydrocarbons which is approximately 36° C. In the case where there was no agitator tool, the heat storage material gradually hardened starting from the outer circumferential section. However in the case where an agitator tool was used, the agitator tool continually moved over a longer period of time compared to the case of no agitator tool, and hardening just on the outer circumferential section did not occur. The time that the heat storage material was held in the vicinity of the melting point or in other words the sustained period, is defined as the difference between the time that the heat storage material temperature drops to 36.4° C., and the time afterward that the temperature is fixed at approximately 36° C., and then drops to 35.5° C. An evaluation using this numerical value was made under each condition.

Figure 5:
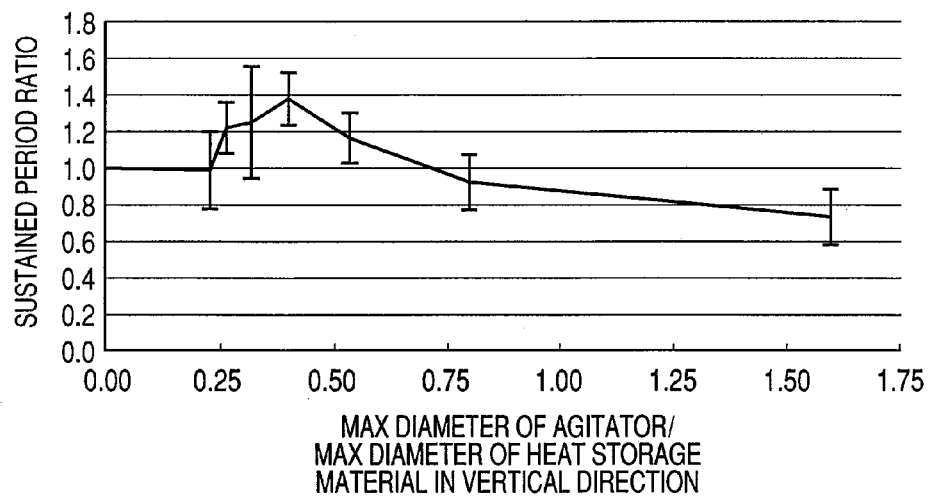
FIG. 5 is a graph showing the time that the heat storage material temperature is maintained in the vicinity of the melting point versus the ratio of agitator tool to heat storage material heights.

FIG. 5 is a graph showing the time that the heat storage material is maintained in the vicinity of the melting point versus the ratio of agitator tool and heat storage material height. The ratio A/B (Max diameter of agitator in vertical direction/max diameter of heat storage material) where A is the maximum diameter of the agitator tool vertically and B is the maximum diameter of the container was evaluated. The sustained period when no agitator tool was used is set as the value 1, and the ratio (sustained period ratio) then calculated for each condition. As the ratio A/B between the maximum diameter A of the agitator tool in the vertical direction and the maximum diameter B of the container becomes larger, the quantity of heat storage material sealed within the container becomes smaller and the sustained period becomes shorter. If the ratio A/B between the maximum diameter A of the agitator tool in the vertical direction and the maximum diameter B of the container drops to 0.75 or less, then the sustained period drastically increases due to the agitator tool and the sustained period can be maintained longer than when no agitator tool is used. When using the ratio C/D consisting of the agitator tool volume C and the container internal volume D to make an evaluation, the sustained period can be maintained longer than when no agitator tool is used, if the ratio C/D is $6.7 \times 10^{-2}$ or lower.

Figure 6:
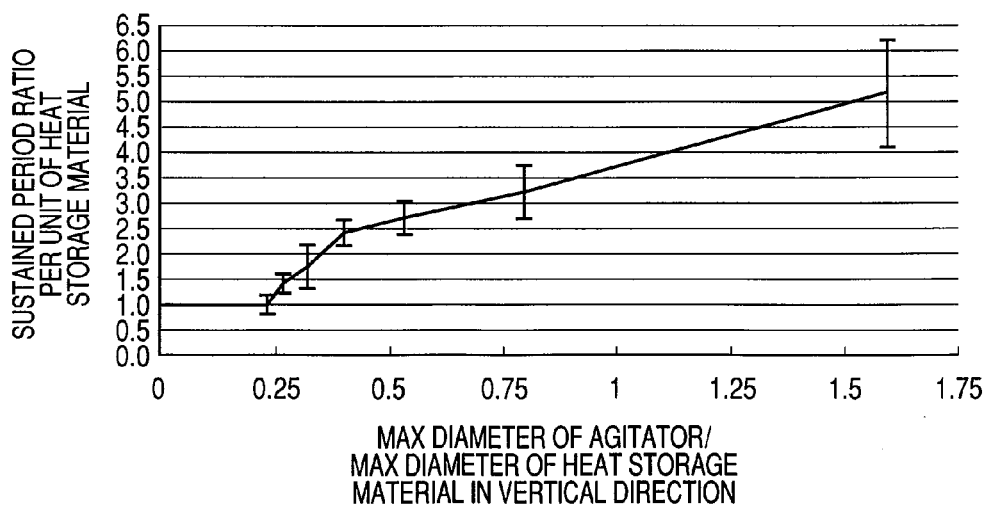
FIG. 6 is a graph showing the sustained period that the heat storage material temperature is maintained in the vicinity of the melting point per unit of heat storage material relative to the agitator tool to heat storage material height ratio.

FIG. 6 is a graph showing the time that each unit of heat storage material temperature is maintained in the vicinity of the melting point relative to the agitator tool and heat storage material height ratio. The ratio A/B (maximum diameter of agitator tool in vertical direction/max diameter of heat storage material) where A is the maximum diameter of the agitator tool vertically and B is the maximum diameter of the container was evaluated. To find the sustained period per unit of heat storage material, the sustained period when no agitator tool was used was set as the value 1, and the ratio (sustained period ratio per unit of storage material) then calculated for each condition. As the ratio A/B for the maximum diameter A of the agitator tool in the vertical direction and the maximum diameter B of the container becomes larger, the agitation of the heat storage material becomes more efficient and the temperature uniformity improves. The time that each unit of heat storage material can be maintained can consequently be extended. The sustained period increases to 50 percent or higher if the ratio A/B reaches 0.3 or more. When using the ratio C/D consisting of the agitator tool volume C and the container internal volume D to make an evaluation, the sustained period can be increased to 50 percent or higher if the ratio C/D is $4 \times 10^{-2}$ or more.

Results from FIG. 5 and FIG. 6 show in particular that when adjusting the height ratio of the heat storage material and the agitator tool, the sustained period for maintaining the temperature of the heat storage material in the vicinity of the melting point can definitely be increased. If the ratio A/B for the maximum diameter A of the agitator tool and the maximum diameter B of the container oriented vertically is higher than 0.3 or lower than 0.75, then the sustained period of the heat storage material can be increased to 50 percent or higher. When the A/B ratio equals 0.53 then the sustained period reaches a maximum of 170.6 percent. If the ratio C/D consisting of the agitator tool volume C and the container internal volume D is larger than the $3.4 \times 10^{-2}$ and smaller than $6.7 \times 10^{-2}$, then the sustained period of the heat storage material will increase by the same 50 percent or more. When the ratio C/D equals $4.5 \times 10^{-2}$, then the sustained period reaches a maximum of 170.6 percent.

Figure 7:
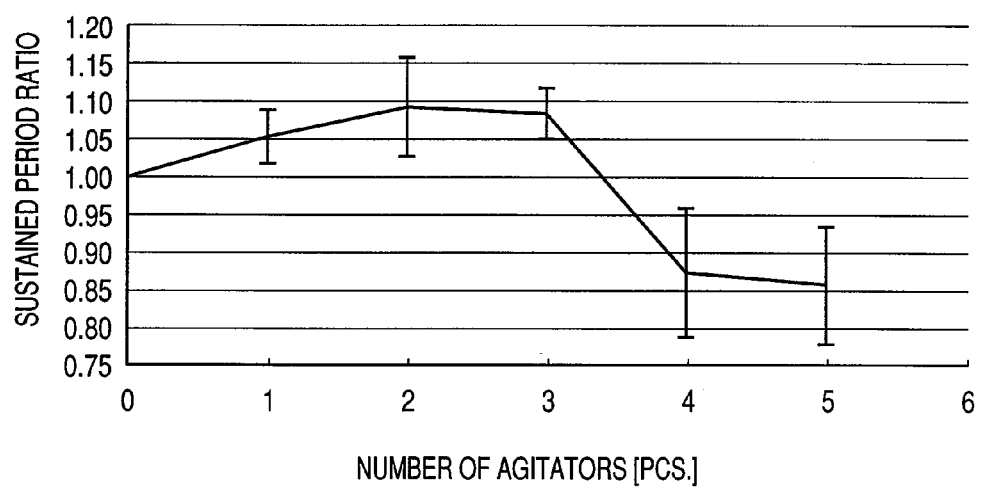
FIG. 7 is a graph for evaluating the change in the (temperature) sustained period when the number of agitator tools is changed.

FIG. 7 is a drawing showing the changes in the sustained period when maintaining the temperature of the heat storage material in the vicinity of the melting point when the number of agitator tools is changed. The agitator tool is a sphere of glass material and approximately 1.6 cm in diameter the same as in the FIG. 4. The number of agitator tools was set to 0, 1, 2, 3, 4 and 5. Here, n-Eicosane which is expressed chemically as $C_{20}H_{42}$ and has a melting point of 36.4° C. is utilized as the hydrocarbons sealed within the container and serving as the heat storage material. The bottom surface of the container holding the heat storage material was circular and approximately 4.5 cm in diameter, and the height of the heat storage material in the container was set at 6 cm. The heat storage material was heated beforehand to 45° C. by a thermostat to liquefy the hydrocarbons to form a liquid, and then was placed in a state where a rotational motion and gentle gradient were applied under an outside temperature of 32° C. During this period, the temperature sensor measured the temperature fluctuations in the upper part of the heat storage material, and changes over time in the upper section temperature as well as the state of the hardened heat storage material were assessed. The sustained period was defined and calculated the same as in FIG. 4. The value for the sustained period when no agitator tool was inserted was set as 1, and the ratio (resolved time ratio) calculated for each condition.

As can be seen in the figure, the larger the number of agitator tools, the larger the agitating current inside the container became. The sustained period also increased along with the larger number of agitator tools. The surface area at the bottom of the container on the other hand became smaller with a larger number of agitator tools, so that the agitator tools possessed less freedom of movement. In this case, the amount agitator tool motion sharply decreased when the number of agitator tools was increased to four, and the sustained period decreased inversely (to the number of agitator tools). When two or three agitator tools were used, then the sustained period rate increased respectively 3.8 percent and 3.0 percent compared to when only one agitator tool was used.

Figure 8:
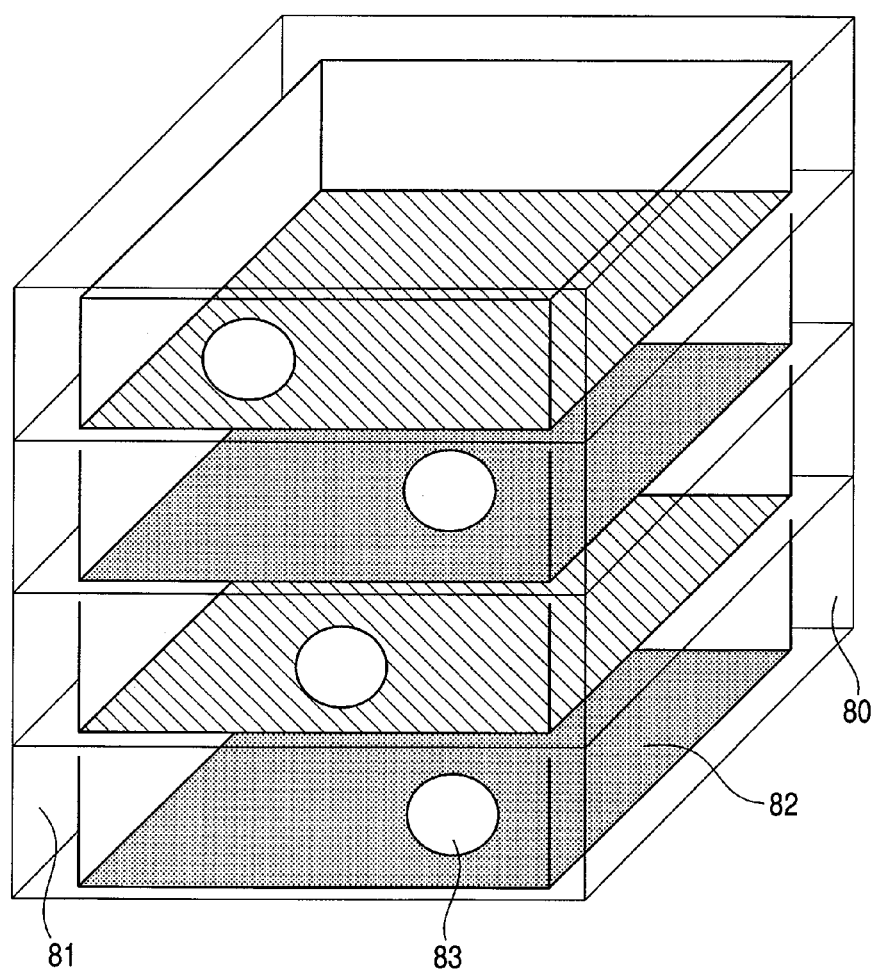
FIG. 8 is an overall structural view showing the temperature regulating members containing agitator tools stacked on each other vertically.

FIG. 8 shows an example of a structure where the temperature regulating members containing the agitator tools are stacked vertically on each other. In the example, four temperature regulating members are stacked together. If the ratio A/B for the maximum diameter A of the agitator tool and the maximum diameter B of the container oriented vertically is 0.3 or higher and 0.75 or lower, or if the ratio C/D consisting of the agitator tool volume C and the container internal volume D is $3.4\times10^{-2}$ or larger and $6.7\times10^{-2}$ or smaller, then the same effect as described above is achieved.

Each container structure includes a high heat propagation film 80, and a heat insulator wall 81. A heat storage material 82 and an agitator 83 are installed inside the container structure. During shipping, the high heat propagation film 80 reaches a state in contact with the culture vessel holding the cells, and heat is conveyed via the high heat propagation film 80, the temperature inside the culture vessel is maintained at approximately 36° C. The heat insulating effect of the heat insulator wall 81 suppresses the discharge of heat from all other locations so wasteful heat discharge is prevented. An agitator tool 83 is installed inside the container. The container in this figure utilizes one agitator tool but multiple agitator tools may be utilized the same as the case shown in FIG. 2.

Figure 9:
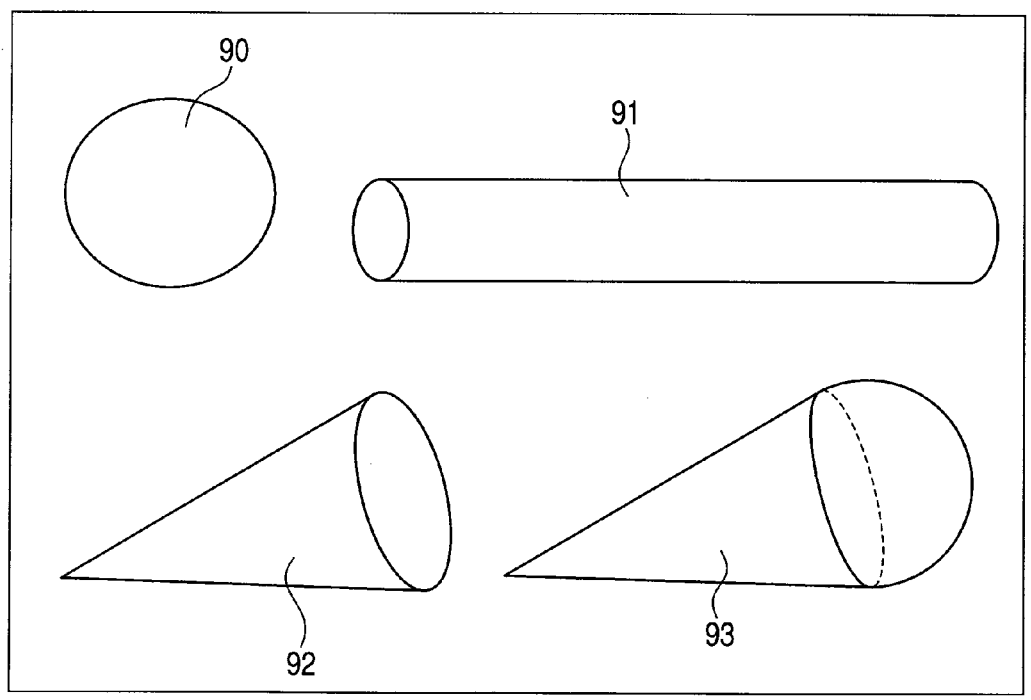
FIG. 9 is a drawing showing agitator tool shapes.

FIG. 9 shows typical agitator tool shapes. The agitator tool is made in a shape that allows easily changing position within the heat storage material. An agitator tool 93 combines a cone and sphere in a cubic shape that is a combination of a spherical agitator tool 90, a cylindrical agitator tool 91, and a conic agitator tool 92. The spherical agitator tool 90 is able to change its relative position most easily within the interior of the heat storage material.

Figure 10:
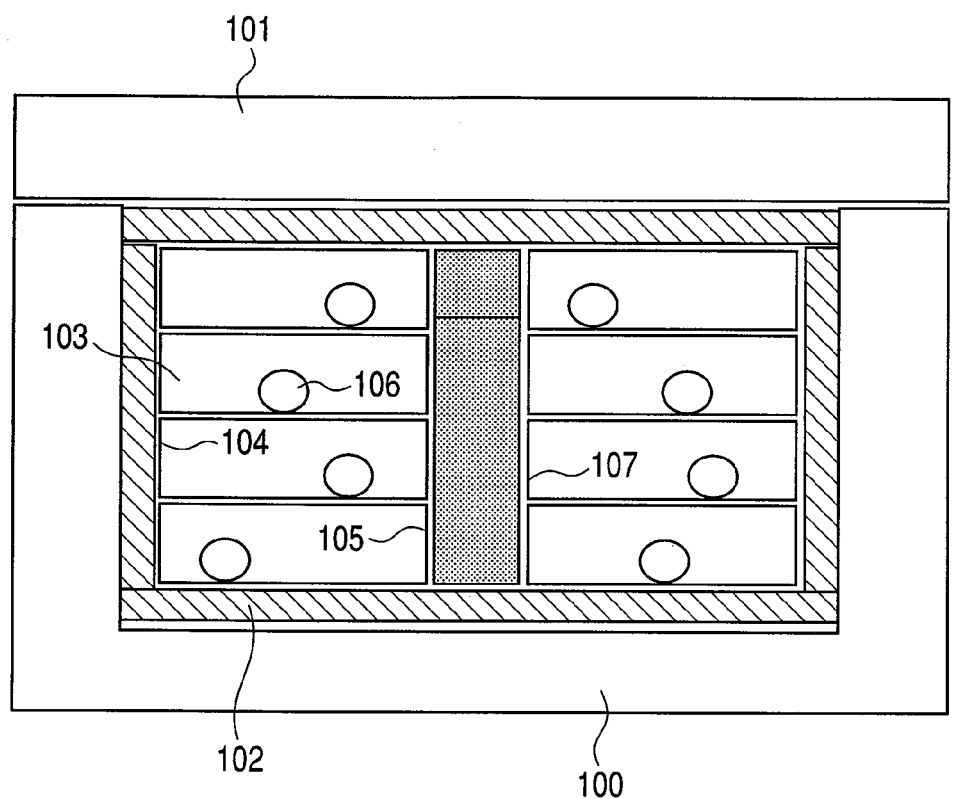
FIG. 10 is a drawing showing the structure of the portable homothermal container.

FIG. 10 shows the tube-shaped culture vessel inside the portable homothermal container made from the temperature regulating member and heat insulator section. Here, the temperature regulating members (containers) whose structure is made from heat storage material and agitator tools are stacked vertically in multiple units. The total height of the multiple stacked heat storage material, or in other words the multiple temperature regulating members is set to the approximate height of the tube culture vessel. One or multiple agitator tools are installed within the respective heat storage material. Agitator tool movement within the heat storage material causes an agitating current in the interiors of all the stacked temperature regulating members (containers), and eliminates thermal non-uniformities within the interior. Consequently, the integrated, stacked heat storage material is capable of eliminating thermal non-uniformities within the interior whether in the upper portion or the lower portion.

The transport container is made from an outer container 100 and a lid 101. A heat insulator section 102 is installed inside the outer container 101, and serves to prevent heat from leaking outwards. The reference numeral 103 is the heat storage material enclosed by a heat insulator wall 104 and a high heat propagation film 105 for conveying heat and possessing expansion/contraction properties. The reference numeral 106 denotes the agitator tool. The high heat propagation film 105 functions as a container for storing the heat storage material and the agitator tool. Containers holding the heat storage material and the agitator tool are stored stacked in four levels. If the ratio A/B for the maximum diameter A of the agitator tool and the maximum diameter B of the container oriented vertically is 0.3 or higher and 0.75 or lower; or if the ratio C/D consisting of the agitator tool volume C and the container internal volume D is $3.4\times10^{-2}$ or larger and $6.7\times10^{-2}$ or smaller, then the same effect as described above can be achieved. A tube culture vessel 107 whose interior contains for example cells, is stored inside the heat container holding the heat storage material. The culture vessel makes contact by way of the high heat propagation film 105 so that the heat storage material in a liquid state functions as a cushioning member besides maintaining the temperature via the heat storage material. When the culture vessel makes contact with the heat storage material by way of the high heat propagation film 105 of the container on the side surface in the longitudinal direction and preferably in applicable side surface that is essentially the entire surface, then the temperature maintenance and cushioning effects can be further enhanced.

The section of the temperature regulating member (container) holding the heat storage material and making contact with the tube culture vessel is capable of expanding and contracting and may even be a film that can clamp the culture vessel in position. The sections making contact with tube culture vessel and the section where the heat storage material makes mutual contact are a material with high heat propagation, and a heat insulating material may be used in all other sections. The efficiency that the heat propagates to the cells may in this case be adjustable. Material such as glass or iron may be used for the agitator tool.

What is claimed is:

1. A transportable holding container comprising:
   an outer container configured to house a culture vessel and a plurality of containers therein,
   a heat storage material constituted so as to undergo a liquid-to-solid phase transition at a given temperature inside each of said plurality of containers, and
   a plurality of agitator tools disposed so as to be in contact with the heat storage material for stirring up the heat storage material inside said plurality of containers, wherein each of said plurality of containers contains at least one of said plurality of agitator tools,
   wherein the agitator tools are freely movably embedded in the heat storage material so as to stir up the heat storage material by freely changing their relative positions in the heat storage material solely by movement of the container in which each is contained during transport without using a drive device,
   wherein the ratio A/B for the maximum diameter A of the agitator tool and the maximum diameter B of its container oriented vertically, for at least one of said agitator tools in each of said plurality of containers, is $0.3 \leqq A/B \leqq 0.75$,
   wherein each of said plurality of containers has a heat propagation film, which conducts heat from the heat storage material to the culture vessel, having elasticity and configured to secure a position of the culture vessel by being stacked in the outer container, and
   wherein the culture vessel contacts the heat storage material through the heat propagation film.

2. A transportable holding container according to claim 1, wherein the ratio C/D consisting of the agitator tool volume C and the container internal volume D of the container containing said agitator tool having the agitator too volume C, for at least one of said plurality of agitator tools in each of said plurality of containers, is $(3.4\times10^{-2}) \leqq C/D \leqq (6.7\times10^{-2})$.

3. The transportable holding container according to claim 1, wherein the heat storage material is paraffin.

4. The transportable holding container according to claim 3, wherein the paraffin is n-Eicosane.

5. The transportable holding container according to claim 1, wherein each of the agitator tools is made from either glass or iron.

6. The transportable holding container according to claim 1, wherein the agitator tool surfaces essentially do not react chemically with the paraffin.

7. The transportable holding container according to claim 1, wherein each of the plurality of containers includes a heat insulator section and a heat propagation member section.

8. The transportable holding container according to claim 1, wherein each of said plurality of containers comprises a heat insulator section installed to enclose the container.

9. A transportable holding container according to claim 1, wherein sections of the plurality of containers making contact with the culture vessel and the sections where the heat storage material makes mutual contact include a material with the heat propagation film, and a heat insulating material to be used in all other sections.

* * * * *